(12) United States Patent
Porat

(10) Patent No.: US 6,234,448 B1
(45) Date of Patent: May 22, 2001

(54) PINCH CLAMP

(75) Inventor: Gad Porat, Jerusalem (IL)

(73) Assignee: Medivice Systems Ltd., Jerusalem (IL)

( * ) Notice: Subject to any disclaimer, the term of this patent is extended or adjusted under 35 U.S.C. 154(b) by 0 days.

(21) Appl. No.: 09/439,850

(22) Filed: Nov. 12, 1999

(30) Foreign Application Priority Data

Nov. 12, 1998 (IL) ..................................................... 127029

(51) Int. Cl.[7] .................................................... F16K 7/04
(52) U.S. Cl. .................................................. 251/10; 251/9
(58) Field of Search ...................................... 251/4, 9, 10

(56) References Cited

U.S. PATENT DOCUMENTS

| | | | |
|---|---|---|---|
| D. 283,918 | 5/1986 | Jacobson | 251/10 |
| 3,461,876 | 8/1969 | Miller, Jr. | 251/10 |
| 3,822,052 | 7/1974 | Lange | 251/10 |
| 3,942,228 | 3/1976 | Buckman et al. | 251/10 |
| 4,097,020 | 6/1978 | Sussman | 251/10 |
| 4,588,160 | 5/1986 | Flynn et al. | 251/10 |
| 5,174,477 | 12/1992 | Schafer | 251/10 |
| 5,203,056 | 4/1993 | Funk et al. | 251/10 |
| 5,318,546 | 6/1994 | Bierman | 604/250 |
| 6,113,062 | 9/2000 | Schnell et al. | 251/10 |

FOREIGN PATENT DOCUMENTS

| | | |
|---|---|---|
| 88 12 121 | 1/1989 | (DE) . |
| 0 799 627 A2 | 10/1997 | (EP) . |

Primary Examiner—Kevin Shaver
Assistant Examiner—D A Bonderer
(74) Attorney, Agent, or Firm—Seed IP Law Group PLLC

(57) ABSTRACT

A pinch clamp for enabling a collapsible tube to be pinched so as to prevent fluid from flowing within a lumen in the tube. The clamp is mountable onto the tube in a lateral direction and is adapted for use with tubes having diameters within a predetermined range. Means are provided for preventing the clamp from disengaging from the tube when in the unclamped position.

20 Claims, 7 Drawing Sheets

PINCH CLAMP

FIELD OF THE INVENTION

The present invention relates to a tube clamping device, in particular a pinch clamp device for selectively closing off and opening the lumen of resilient tubing.

BACKGROUND AND PRIOR ART

Pinch clamp devices are well known and have been used successfully for many years in the medical field and in research laboratories for regulating by a simple one-hand operating action the flow of fluids in flexible tubing, particularly to and from patients. Pinch clamp devices are essentially flow control devices or clamps for use with a length of resilient collapsible tube or tubing, wherein fluid flow through the tube may be selectively enabled and stopped, and in some cases regulated, by means of a pair of opposed clamping abutments acting on the tube, without contact between the device and the fluid.

Most of these devices suffer from the disadvantage that the tubing has to be inserted into the clamping device in a longitudinal manner, i.e., the tube has to be threaded into the clamp endwise. Since this type of tubing generally comprises fixed end connectors and/or equipment and/or fixtures, and in fact commercially available tubing is rarely obtainable without such connectors, equipment and/or fixtures, it is not possible, nor in any event practical, to mount the device onto the tubing once the end connectors have been fixed, particularly when the tubing is connected to other equipment and/or the patient. Thus lengths of tubing comprising a clamping device mounted thereon are typically assembled and marketed as a set, which tends to be significantly more expensive than the sum of the cost of a clamp plus the cost of a similar set minus the clamp, thereby contributing to health care and insurance expenses. Furthermore, there are many instances where a simple tube with end connectors is required, or when only say one of the tubes in a bifurcated tube, for example, needs to be clamped, and as such similar tubes provided with a full complement of clamps are unnecessary and therefore add expense to the medical treatment being provided. The alternative of using a one-way stopcock, mounted on-site by professional medical staff when the tube does not comprise a clamp, is significantly expensive and also increases healthcare costs.

There are also applications where clamps are not generally pre-mounted onto tubing, as in the case, for example, of catheters. In such applications, it may nevertheless be advantageous to clamp the tube at some point prior to retrieving the tube from the body. For example, on site clamping can also prevent spillage of liquid contamination at the open ends of tubes, drains and catheters (pippet effect), such as in urology, gastric zonds, etc., when these are removed from a patient or when the vacuum system is closed. However, it is not possible to insert a conventional pinch clamp longitudinally onto the tube/drain/catheter, once inserted into the body. In such cases, the provision of a clamp which can be laterally mounted onto the pipe/drain/catheter would be considerably advantageous.

U.S. Pat. No. 4,588,160 to Flynn et al. and U.S. Pat. No. 3,942,228 to Buckman et al. each discloses a tube clamping device which includes a pair of arms with tube clamping means thereon which are movable from an open position to a latched, closed position in which the clamping means effects occlusion of a tube passing through the clamp. Each arm has a slot extending into the sidewall of the arm so that the tube can be laterally inserted and removed from the clamping device.

However, in both these references the lateral slot for laterally inserting the tube onto the device is closely correlated to the size of the tubing. Thus, the clamp cannot be used with larger diameter tubing, and furthermore, smaller diameter tubes would easily fall out of the clamp when in the unclamped position. As such, a potential user requires as many different sized clamps as he has different sized tubing, which is economically as well as logistically disadvantageous.

One aim of the present invention is to overcome the aforementioned disadvantages of the prior art pinch clamp devices.

It is another aim of the present invention to provide a pinch clamping device which may be laterally mounted onto a length of tubing.

In particular, it is an aim of the present invention to provide a pinch clamping device which may be mounted onto a piece of resilient tubing which comprises end connectors or which cannot be disconnected from other equipment.

It is also an aim of the present invention to provide a pinch clamping device which may be mounted onto a piece of resilient tubing which is indwelling in a body.

It is another aim of the present invention to provide a pinch clamping device which may be mounted onto a piece of resilient tubing which is indwelling in a body.

It is another aim of the present invention to provide a pinch clamping device which may be positively mounted onto resilient tubing and which is substantially prevented from accidentally coming off the tubing when in the unclamped position.

The present invention achieves these and other aims by providing a pinch clamping device comprising a pair of longitudinal arms with tube clamping means thereon which are movable from an open position to a latched, closed position in which the clamping means effects occlusion of a tube passing through the clamp. The pinch clamping device is characterized in that the clamping means project laterally from the arms, enabling a length of tubing to be laterally inserted into the device, in-between the clamping means such that with the tubing in place, the device may operate substantially in much the same way as regular prior art pinch clamp devices. The pinch clamping device is also characterized in comprising lateral guard means for preventing the device from being inadvertently or accidentally removed from the tubing, or from simply falling off the tubing, when in the unclamped position.

Thus, by providing a portion of the aligned clamping means laterally extending from the body of the clamp, rather than having slots cut into the clamp, the pinch clamping device is much more versatile than prior art clamps and may be laterally mounted onto tubing comprising a range of diameters. To further ensure that the clamp remains on the tubing even when the tubing is unclamped, and auxiliary catch member and latch means are provided, which when mutually engaged bring the lateral guard means into an overlapping relationship with the facing clamping means, thereby positively trapping the device onto the tubing.

The device of the present invention is thus robust, relatively inexpensive, easy to use, and typically requires a simple one-hand operation for installation onto tubing. After installation, the clamp is operated in much the same fashion as prior art pinch clamps, including the advantage that the clamp does not tend to fall off tubing when not being used.

SUMMARY OF INVENTION

The present invention relates to a pinch clamp device for use with a resilient collapsible tube having an external diameter within a predetermined range of diameters comprising: a U-shaped body comprising a generally longitudinal upper arm and a generally longitudinal lower arm, said arms comprising opposed longitudinal first ends and opposed longitudinal second ends, said second longitudinal ends being joined to a resilient base biased to distance the said first ends of the arms apart by substantially a predetermined first distance, aligned clamping abutments disposed on at least a portion of facing surfaces of said upper and lower arms, said clamping abutments adapted for clamping therebetween a resilient collapsible tube having an external diameter within said predetermined range of diameters, wherein at least part of said aligned clamping abutments project laterally at least with respect to said base by at least a predetermined fourth distance sufficient to enable a resilient tube having an external diameter within said predetermined range of diameters to be clamped between said clamping abutments laterally with respect to said base, said predetermined first distance between said first ends being such as to provide a second distance between said clamping abutments at least equal to the largest diameter of said predetermined range of diameters; at least one first flexible catch arm extending generally upwardly from the first end of said lower arm and comprising at least one catch member, said at least one catch member generally facing said first end of said upper arm, said first catch arm being resiliently connected to said lower arm and biased to maintain at least an upper portion of said first catch arm in at least close proximity to said first end of said upper arm at least when said first ends are at said predetermined first distance apart; latch means on said first end of said upper arm adapted for selective engagement with said catch member when said first ends are at a predetermined third distance from each other, whereupon said second distance between said clamping abutments is correspondingly reduced thereby enabling a tube of a diameter within said predetermined range of diameters held between said clamping abutments to be at least partially collapsed.

Preferably, the said upper arm and said lower arm comprise suitable lateral extensions, wherein said extensions project laterally in the same direction and substantially to the same extend relative to the said base as said clamping abutments. Optionally, said lower arm further comprises at least one second flexible catch arm extending generally upwardly from the first end of said lateral extension of said lower arm and comprising at least one catch member, said at least one catch member generally facing said first end of said upper arm, said second catch arm being resiliently connected to said lower arm and biased to maintain at least an upper portion of said second catch arm in at least close proximity to said first end of said upper arm at least when said first ends are at said predetermined first distance apart, said second catch arm being laterally displaced from said at least one first catch arm to define a slot therebetween having a predetermined width. Preferably, said predetermined width is at least equal to the largest diameter of said predetermined range of diameters. Optionally, the lower longitudinal end of said slot is substantially rounded.

Optionally, said third distance is such as to enable a tube of a diameter within said predetermined range of diameters to be fully collapsed when in-between said clamping abutments, thereby preventing any fluid from flowing through such a tube.

Optionally, said latch means comprises an end surface adapted for selective engagement with said at least one catch member, said latch means and said at least one catch member comprising cooperating cam surfaces on the engaging portions of the said latch means and catch arm, whereby selective movement of said upper arm towards said lower arm causes the catch arm to be cammed outwardly from the latch means enabling the latch means to proceed downwardly below the catch member whereupon the catch arm swings towards the latch means so that the end surface engages the at least one catch member. Further optionally, said catch member comprises an engaging surface for engaging with said end surface of said at least one catch member, said engaging surface being angled in a lateral direction with respect to said upper arm.

Optionally, said clamp further comprises an auxiliary catch member on said at least one first catch arm wherein said latch means on said first end of said upper arm is adapted for selective engagement with said auxiliary catch member when said first ends are at a predetermined first distance from each other, thereby selectively preventing said upper and said lower arms from being spaced apart. The said clamp may further optionally comprise an auxiliary catch member on said second catch arm wherein said latch means on said first end of said upper arm is adapted for selective engagement with said auxiliary each member when said first ends are at a predetermined first distance from each other, thereby selectively preventing said upper and said lower arms from being spaced apart.

Optionally, the pinch clamp further comprises shear prevention means for substantially preventing lateral movement between at least one of said at least one first catch arm and said at least one second catch arm relative to said upper arm. The shear prevention means may comprise a tab at the said first end of said upper arm, said tab being adapted to engage either of the sidewalls of the said slot between said first and said second catch arms. Alternatively, the shear prevention means may comprise a pair of opposed tabs at opposite lateral edges of said first end of said upper arm, each said tab being adapted to respectively engage a corresponding outer lateral edge of the said first and said second catch arms.

Optionally, the said clamping abutments further comprise lateral guard means for preventing a tube of a diameter within said predetermined range of diameters positioned between said clamping abutments From being laterally removed therefrom when said clamping abutments are distanced from each other at said predetermined second distance. The lateral guard means preferably comprises at least one tab element projecting from one said clamping abutment in the direction of the facing clamping abutment, said tab element adapted to laterally overlap said facing clamping abutment when said latch means is engaged with said at least one catch member.

The pinch clamp may also further comprise tube retainment means at said second longitudinal ends. Preferably, said tube retainment means comprises an upper tab and an opposed lower tab, said tabs being resilient and depending from corresponding free edges of the said second longitudinal ends of said upper arm and said lower arm, respectively, said tabs forming an entry section and defining a throat therebetween, said throat not being substantially wider than the maximum diameter of said range of diameters, said opposed tabs and said free edges of said longitudinal ends and a facing lateral edge of said resilient base defining a substantially longitudinal open aperture for receiving a tube having a diameter within said predetermined range of diameters. Preferably, said tabs are in the form of suitable resilient U-shaped leaf springs. Preferably, said tabs substantially follow the profile of a corresponding parallel portion of said resilient base, and the perimeter of the said open aperture is substantially C-shaped.

DESCRIPTION

The present invention is defined by the claims, the contents of which are to be read as included within the disclosure of the specification, and will now be described by way of example with reference to the accompanying Figures.

The present invention relates to a flow control device or clamp, generally designated (10), for sue with a length of resilient collapsible tube or tubing (90), having an external diameter within a predetermined range of diameters, wherein fluid flow through the tube is controlled without contact between the device and the fluid. The said clamp (10) is typically made from a relatively hard though flexible and resilient medically compatible material, preferably a plastic or plastic composition including for example HDPE, nylon, polypropylene, acetal or any other suitable composition. The device (1) is advantageously a single piece or unitary member and is thus typically molded as an integral piece.

Figure 1:
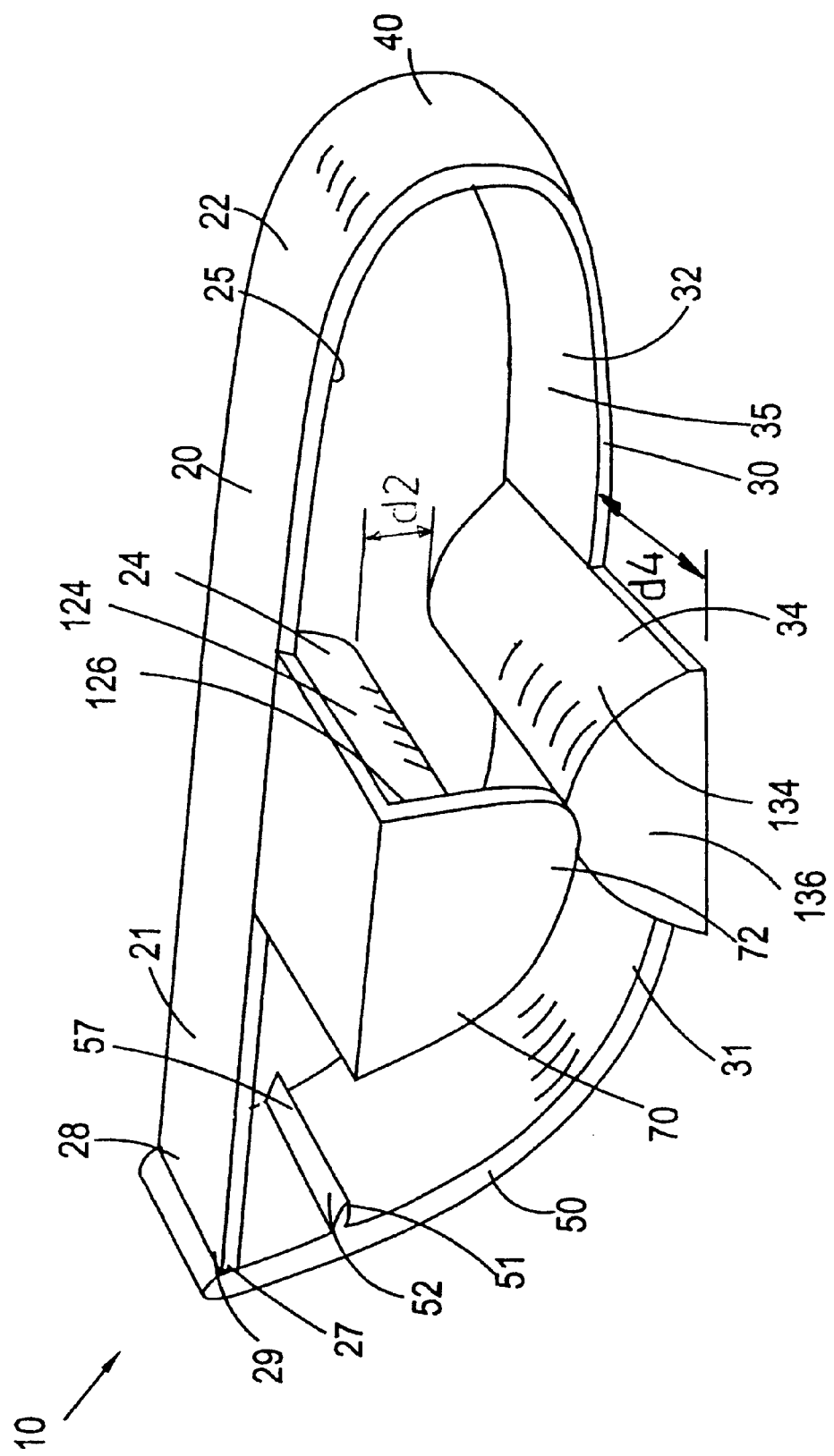
FIG. 1 illustrates, in perspective view, the structural characteristics of a second embodiment of the present invention.
Figure 2:
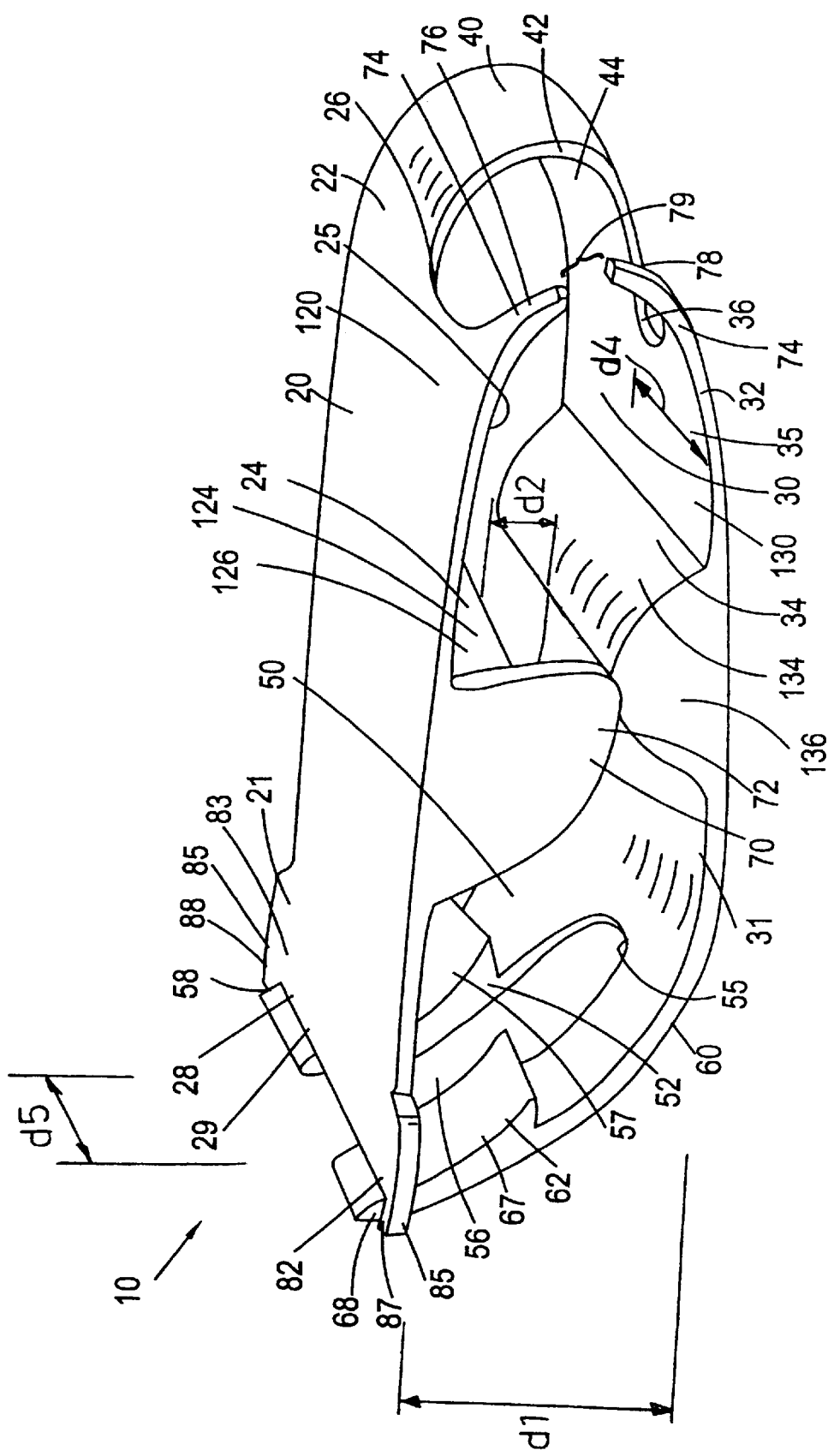
FIG. 2 illustrates, in perspective view, the structural characteristics of a preferred embodiment of the present invention.
Figure 3:
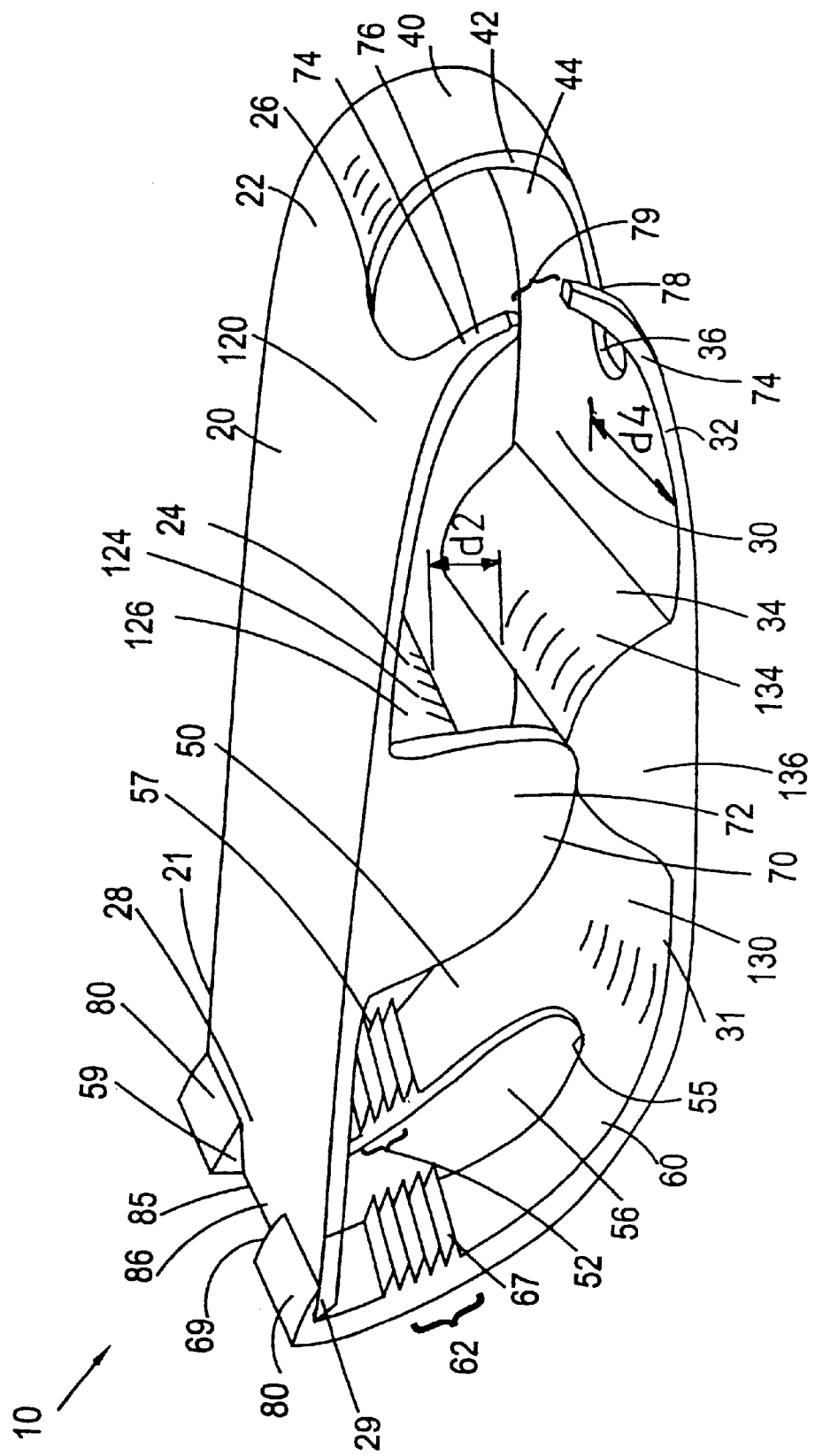
FIG. 3 illustrates, in perspective view, the structural characteristics of a third embodiment of the present invention.
Figure 4:
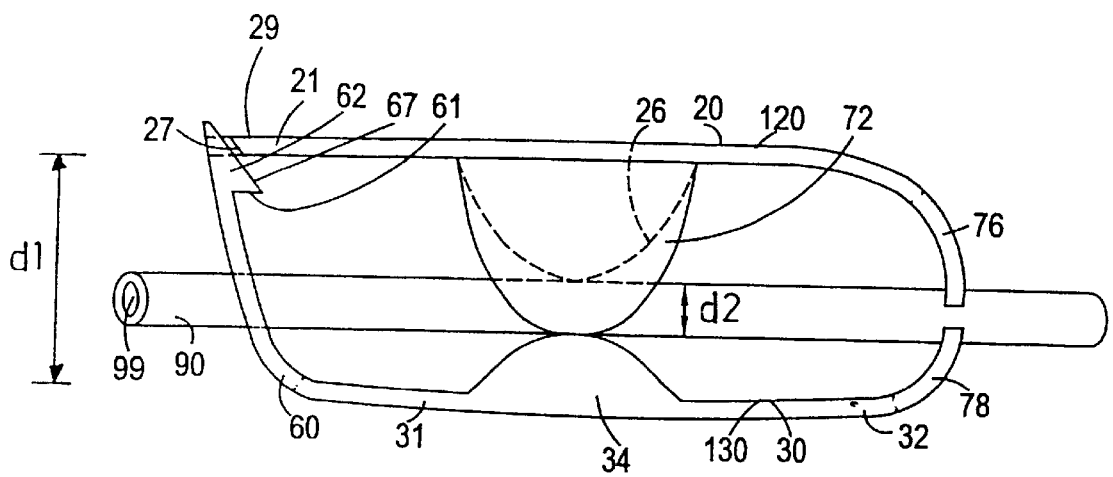
FIG. 4 illustrates, a side view, the embodiment of FIG. 2 in closed configuration.
Figure 5:
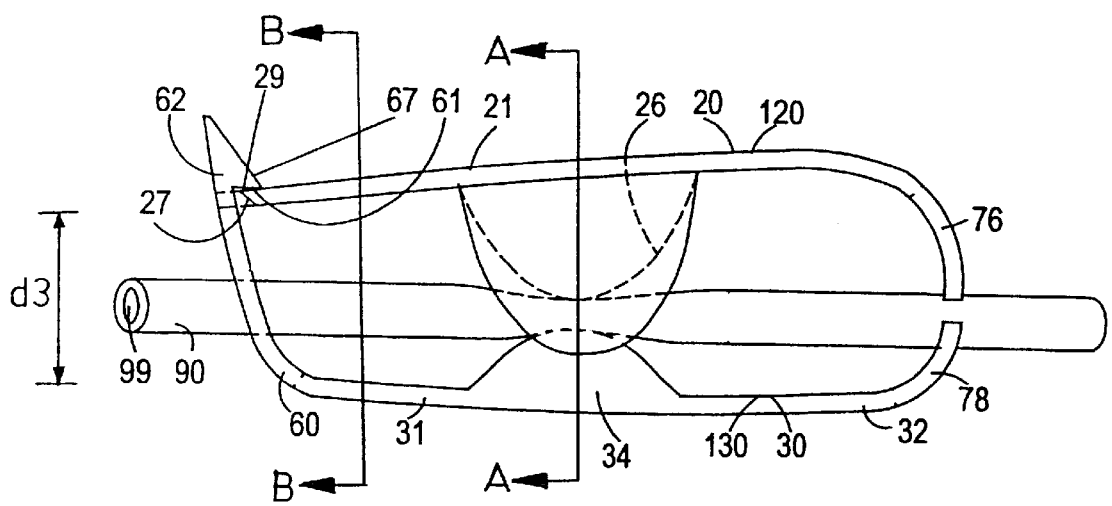
FIG. 5 illustrates, in side view, the embodiment of FIG. 2 in clamped configuration.

FIGS. 2, 4 and 5 illustrate the main features of the preferred embodiment of the present invention, while FIGS. 1 and 3 illustrate the main features of a second and a third embodiment, respectively, of the present invention.

With reference to FIG. 1, the said clamp (10) in the second embodiment of the present invention comprises a generally U-shaped body comprising a generally longitudinal upper arm (20) and a generally longitudinal lower arm (30). The arms (20) and (30) are resilient and comprise opposed longitudinal first ends, (21) and (31) respectively, and opposed longitudinal second ends, (22) and (32) respectively. The second longitudinal ends (22) and (32) are joined to a resilient base (40), typically integrally, the base (40) being biased to distance the said first ends of the arms apart by substantially a predetermined first distance (d1). In other words, the neutral or datum position of the arms relative to one another is such that the said first ends (21), (31) are distanced at said first distance (d1) by virtue of the resilience of the base (40), and the arms (20), (30) may be pulled apart or brought closer together with respect to this datum position.

The clamp (10) further comprises aligned clamping abutments (24), (34) disposed on at least a portion of facing surfaces, (25) and (35) respectively, of said upper and lower arms, (20) and (30) respectively. Alternatively, all of the clamping abutments (24), (34) may actually be laterally displaced with respect to the said base (40), and thus also of any longitudinal parts of the said arms (20), (30). The clamping abutments are typically each in the form of a substantially triangular prism having its base transversely positioned on the surface (25) or (35), with the apex of each of the two facing abutments (24), (34) being somewhat rounded and substantially aligned, or alternatively slightly displaced longitudinally, one with respect to the other. The clamping abutments (24), (34) are adapted for clamping therebetween said tube (90), and the said predetermined first distance (d1) between said first ends (21) and (31) is such as to provide a second distance (d2) between said clamping abutments at least equal to, and preferably greater than, the largest diameter of said predetermined range of diameters, FIG. 1.

The clamp (10) further comprises a first flexible catch arm (50) which extends generally upwardly from the first end (31) of said lower arm (30) and comprises at least one catch member (52) generally facing the first end (21) of said upper arm (20). The first catch arm (50) is resiliently connected to said lower arm (30), preferably integrally, and is biased to maintain at least an upper portion of the said first catch arm (50) in at least close proximity to first end (21) of the upper arm (20), at least when said first ends (21) and (31) are spaced apart at said predetermined first distance (d1). The expression "close proximity" is herein understood as relating to a small dimension with respect to the diameter of the tube (90), and this dimension may even be zero, i.e., the first end (21) of the upper arm may abut against the catch arm (50). The bias of the catch arm (50) with respect to the first end (21) of the upper arm (20) maintains the clamp (10) in a substantially closed configuration when in the unclamped position, and thus assists in preventing the clamp (10) from naturally separating from the tube (90), as hereinafter described in more detail.

The clamp (10) further comprises latch means (28) on said first end (21) of said upper arm (20), adapted for selective engagement with the catch member (52) when said first ends (21) and (31) are at a predetermined third distance (d3) from each other. Thus, when the upper arm (20) and lower arm (30) are brought together such that the distance between the first ends, (21) and (31), is reduced from the said first distance (d1) to the third distance (d3), the gap between the aligned clamping abutments (24), (34), in other words the said second distance (d2), is correspondingly reduced thereby enabling said tube (90) held between said clamping abutments (24), (34) to be at least partially collapsed, thereby correspondingly reducing and even closing the available flow area for the tube (90).

The said latch means (28) typically comprises an end surface (29) adapted for selective engagement with a complementary engaging surface (51) of catch member (52). The latch means (28) and said catch member (52) comprise cooperating cam surfaces, (27) and (57) respectively, on the engaging portions of the said latch means and catch arm. Thus, selective movement of said upper arm (20) towards said lower arm (30) causes the catch arm (50) to be cammed outwardly from the latch means (28) enabling the latch means (28) to proceed downwardly below the catch member (52) whereupon the catch arm (50) swings towards the latch means (28) so that the end surface (29) engages the engaging surface (51) of catch member (52).

The clamp (10) is characterised in that at least part (124), (134) of said aligned clamping abutments (24), (34) project laterally at least with respect to the base (40) by at least a predetermined fourth distance (d4) sufficient to enable said tube (90) having an external diameter within said predetermined range of diameters to be clamped between the clamping abutments (24), (34) laterally with respect to said base (40). Thus, either all or part of the clamping abutments (24), (34) project laterally from the arms (20), (30), at least with respect to the base (40), and preferably also with respect to said catch arm (50). Thus, the said predetermined fourth distance (d4) is optimally approximately equal to the diameter of the tube (90), though it could be smaller or greater.

The clamp (10) is also characterised in that said clamping abutments (24), (34) comprise lateral guard means (70) for preventing the tube (90), positioned between said clamping abutments (24), (34), from being laterally removed therefrom when said clamping abutments (24), (34), in particular said laterally projecting portion of clamping abutments (124), (134), are distanced from each other at said predetermined second distance (d2) when the clamp (10) is in the closed unclamped position.

Said lateral guard means (70) may comprise at least one tab element (72) projecting from one said clamping abutment, (24) or (34), in the general direction towards the facing clamping abutment, (34) or (24) respectively, said tab being located at the free lateral end, (26 or (36) respectively, of said laterally projecting portion of clamping abutments (124), (134). In particular, said tab element (72) is adapted to laterally overlap said facing clamping abutment, (34) or (24) respectively, when said latch means (28) is engaged with said at least one catch member (52).

Figure 6A:
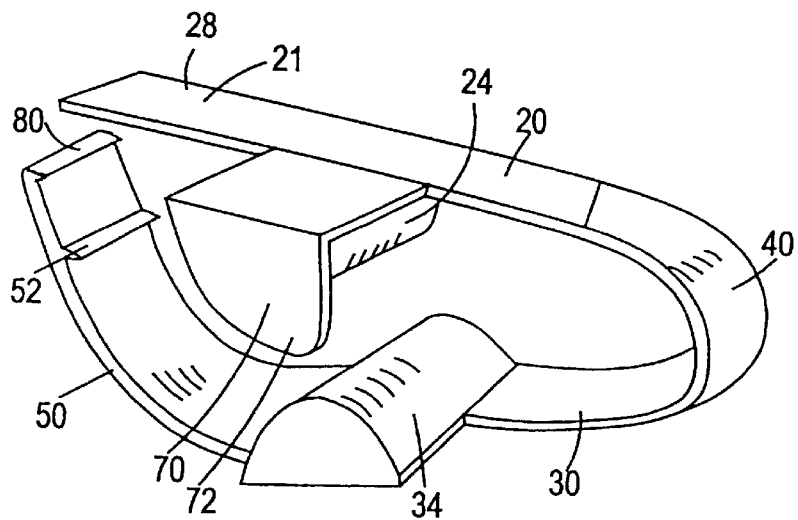
FIG. 6 illustrates, in perspective view, the operation of the embodiment of FIG. 1–FIG. 6(a)—clamp in the open configuration, FIG. 6(b)—clamp in the closed configuration.
FIG. 6(c)—clamp in the clamped configuration.
Figure 6B:
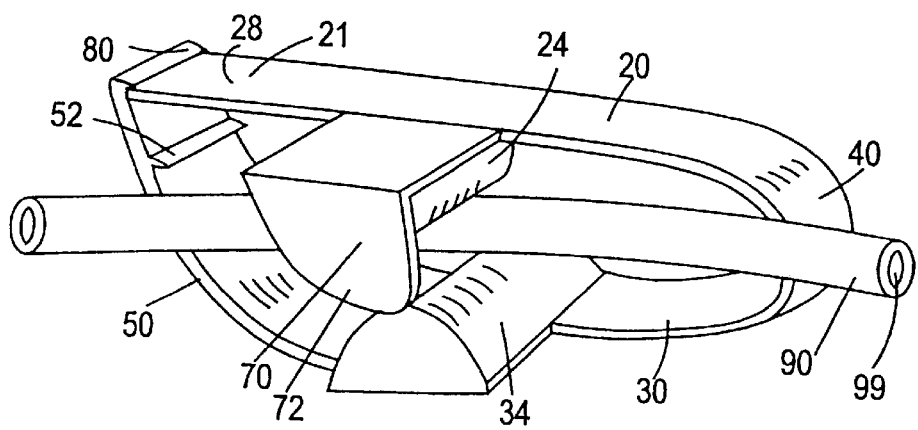
Figure 6C:
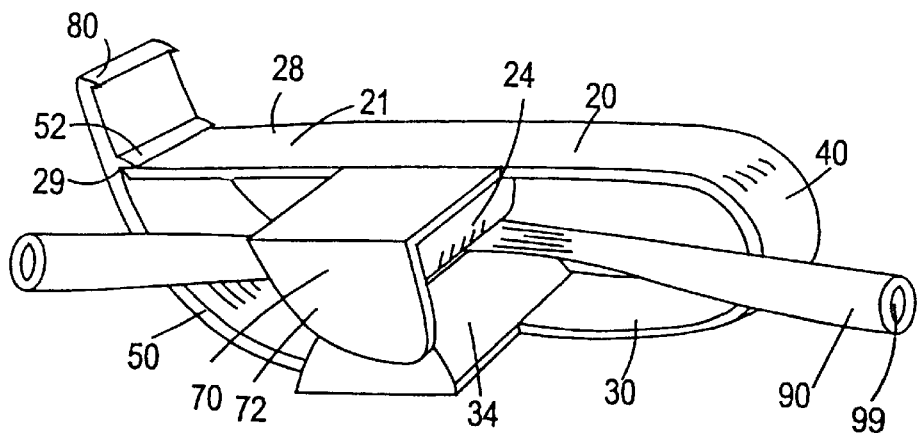

Optionally, and as illustrated in FIG. 6, said clamp (10) may further comprise an auxiliary catch member (80) on said at least one first catch arm (50). The said latch means (28) on said first end (21) of said upper arm (20) is also adapted for selective engagement with said auxiliary catch member (80) when said first ends, (21) and (31), are approximately at said predetermined first distance (d1) from each other, thereby preventing said upper and said lower arms, (20) and (30) respectively, from being spaced apart. Said auxiliary catch member (80) is typically similar to said catch member (50) in form and operation, *mutatis mutandis*.

In the second embodiment of the present invention, and with reference to FIG. 6, the clamp (10) may be used as follows. To mount the clamp (10) onto suitable tubing, the upper and lower arms (20), (30) are first pulled apart until the lateral guard means (70), typically the said tab element (72) is sufficient clear from the opposed clamping abutment (in FIG. 6, he lower clamping abutment (34)) such that the tube (90) may be laterally in between the clamping elements (24), (34), FIG. 6(*a*). Of course, the tab element (72) in practice need only clear the opposed clamping abutment (34) by approximately twice the thickness of the tube (90), since the latter, being flexible, may be squeezed together by hand in order to urge it into the clamp through the gap so created. The resilience of the base (4) returns the upper and lower arms (20) and (30) to their original relative positions, with the first end (21) of the upper arm in close proximity to the catch arm (50). If the catch arm is provided with said auxiliary catch member (80), then this is disengaged from the latching means (28) prior to pulling apart the upper and lower arms (20), (30). Then, after the clamp (10) is mounted onto the tubing (90), the auxiliary catch member (80) is re-engaged with the latching means (28) by bringing the upper and lower arms (20), (30) towards each other sufficiently such that the catch arm (50) is cammed outwardly from the latch means (28) enabling the latch means (28) to proceed downwardly below the auxiliary catch member (80), whereupon the catch arm (50) swings towards the latch means (28) so that the end surface (29) engages the auxiliary catch member (80), FIG. 6(*b*). In this closed, but unclamped position, the tube (90) is loosely held between the clamping abutments (24), (34), and is prevented from being laterally removed from the clamp (10) by the lateral guard means (70) on one side, and by the substantially closed main body of the clamp (10) bounded by the said upper arm (20), base (40), lower arm (30) and catch arm (50). When it is desired to clamp the said tube (90), and thereby to restrict any possible flow therethrough, the said upper arm (20) is moved towards said lower arm (30) causing the catch arm (50) to be cammed outwardly from the latch means (28) enabling the latch means (28) to proceed downwardly below the catch member (52) whereupon the catch arm (50) swings towards the latch means (28) so that the end surface (29) engages the catch member (52), FIG. 6(*c*). To remove the tube (90) from the clamp (10) of the second embodiment, the catch arm (50) is pulled away from the said first end (21) of the upper arm (20) to disengage the latch means (28) from the catch member (52). The arms (20) and (30) are then pulled apart sufficiently to allow the tube to be laterally removed from the clamping abutments, in particular through the gap between the tab (72) and the opposed clamping abutment (34).

A preferred embodiment of the present invention, illustrated in FIG. 2, comprises the same elements and features as the second embodiment as hereinbefore described, *mutatis mutandis*. In the preferred embodiment of the present invention the upper arm (20) and the lower arm (30) optionally comprise suitable lateral extensions (120), (130) respectively, which project laterally in the same direction and substantially to the same extend to the said base (40) as said laterally projecting portion of clamping abutments (124), (134), as is illustrated in FIG. 2, thereby providing said second ends (22) and (23) of the laterally extended arms (20), (30) with free edges, (26) and (36) respectively, laterally adjoining said base (40). Preferably, said extensions (120) and (130) are integral with said arms (20) and (30), respectively.

In the said preferred embodiment of the present invention, the said lower arm (30) further optionally comprises at least one second flexible catch arm (60) extending generally upwardly from the first end (31) of said lower arm (30). Said second catch arm (60) is similar to said first catch arm (50) and comprises at least one catch member (62), generally facing said first end (21) of said upper arm (20). The said second catch arm (60) is resiliently connected to said lower arm (30) and is biased to maintain at least an upper portion of said second catch arm in at least close proximity to said first end (21) of said upper arm (20), at least when said first ends (21), (31) are at said predetermined first distance (d1) apart. The said second catch arm (60) is laterally displaced from said first catch arm (50) to define a slot (56) therebetween having a predetermined width (d5). Advantageously, the said predetermined width (d5) is at least equal to, and preferably greater than, the largest diameter of said predetermined range of diameters. Thus, one end of the tube (90) may be accommodated in the slot (56) as shown in FIG. 2, further ensuring that the clamp (10) remains on the tubing

(90) even when the clamp is in the unclamped configuration. Optionally, and preferably, the lower longitudinal end (55) of said slot (56) is substantially rounded.

For the preferred embodiment, the said predetermined fourth distance (d4) analogous to the said width (d5) of the slot (56) and is thus approximately equal to the diameter of the tube (90), though it preferably greater than, and possibly also smaller than, the diameter of the tube (90). Preferably, though, the said clamping abutments (24), (34) extend through the full lateral width of the clamp (10).

The said end surface (29) of the said latch means (28) is also adapted for selective engagement with catch member (62). The latch means (28) and said catch member (62) comprise cooperating cam surfaces, (27) and (67) respectively, in the engaging portions of the said latch means and catch arm. Thus, selective movement of said upper arm (20) towards said lower arm (30) causes the catch arms (5) and (60) to be cammed outwardly from the latch means (28) enabling the latch means (28) to proceed downwardly below the catch members (52) and (62) whereupon the catch arm (50) swings towards the latch means (28) so that the end surface (29) engages the engaging surfaces (51), (61) respectively of catch members (52) and (62) respectively.

As hereinbefore described, each of the first catch arm (50) and second catch arm (60) may have at least one catch member, (52) and (62) respectively, for engaging with the latch means (28). When the said catch arms (50), (60) only comprise a single catch member (52), (62) respectively, the said third distance (d3) is set such that the distance (d2) between the said clamping abutments (24), (34) is substantially reduced to the extent of ensuring that the tube (90) is totally collapsed between the clamping elements (24), (34), thereby interrupting any possible flow through the now-closed lumen (99) of the tube (90) (FIGS. 4, 5).

In the preferred embodiment, said lateral guard means (70) may comprise at least one tab element (72) projecting from one said clamping abutment, (24) or (34), in the general direction towards the facing clamping abutment, (34) or (24) respectively, said tab being located at the free lateral end, (26) or (36) respectively, of said lateral portion (124), (134) of said clamping abutments (24), (34). In particular, said tab element (72) is adapted to laterally overlap said facing clamping abutment, (34) or (24) respectively, when said latch means (28) is engaged with at least one of said at least one catch member (52) or (62).

Since the laterally projecting portions (124) and (134) of the clamping abutments (24), (34) respectively, are laterally displaced with respect to the base (40), there may be a tendency for these portions (124), (134) to be more distanced apart then other portions of the abutments members (24), (34) which are on the arms (20) and (30) themselves. This is particularly so when the tube (90) is clamped between the portions (124), (134), but also when the tube is clamped in the portion of the clamping portions (24), (34) in-between the arms (20), (30). Thus, to overcome any possible tendency for the clamping abutments (24) and (34) from diverging the said base (40) may be stiffened by increasing the thickness thereof, and optionally also of said second ends (22) and (32) of arms (20) and (30), respectively. Optionally or additionally, suitable ribs or webs may be provided between said base (40) and said arms (20), and (30).

Figure 8A:
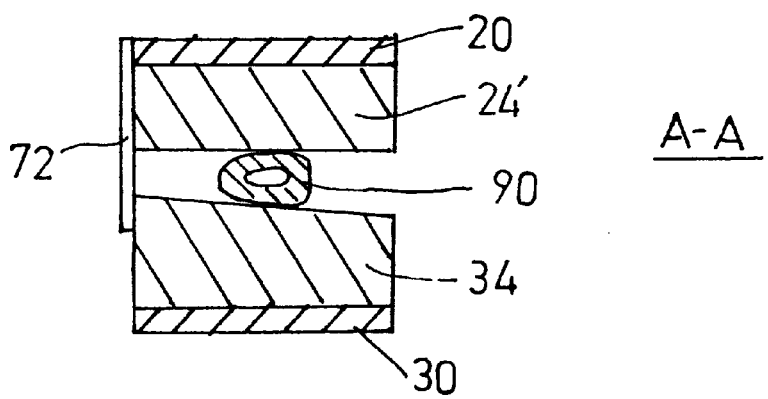
FIGS 8(a) and 8(b) illustrate, in transverse cross-sectional view, alternative clamping abutments arrangements for the embodiment of FIG. 5 taken along A—A.
Figure 8B:
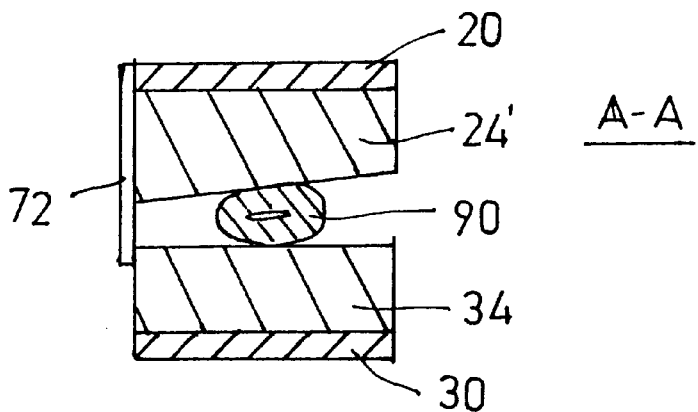

Further optionally, and referring to FIGS. 8(a) and 8(b), the potential tendency for the arms (20) and (30) to diverge may be addressed by having one or either (or indeed both) of said clamping, abutments so configured as to present a laterally diminishing fourth distance (d4) in a lateral direction towards the said portions (124), (134). Thus, in FIG. 8(a), the said clamp (10) comprises a lower clamping abutment (34') which rather than being substantially parallel to the upper clamping abutment (24), has an upper profile at an angle to the lower surface of the upper clamping abutment (24), resulting in a laterally converging slot between the clamping elements (24), (34'). In FIG. 8(b) a similar arrangement is illustrated, in which the upper clamping means (24') has been modified in order to provide a laterally converging slot between the clamping elements (24'), (34). Of course, the clamp (10) may also be configured with clamping abutments (24') and (34'), which are both angled laterally with respect to said surfaces (25) and (35), respectively.

Figure 9:
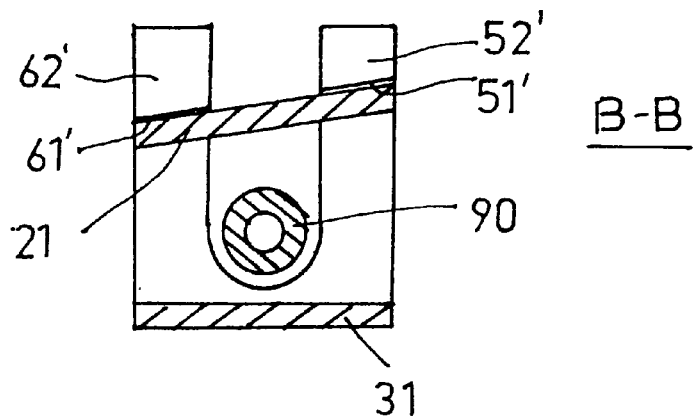
FIG. 9 illustrates, in transverse cross-sectional view, alternative catch member arrangement for the embodiment of FIG. 5 taken along B—B.

Further optionally, and referring to FIG. 9, the potential tendency for the arms (20) and (30) to diverge may also be addressed by comprising catch members (52'), (62') having angling engaging surfaces (51') and (61') with respect to said first end (21) of arm (20), such as to bias the portions (124), (134) closer together than the rest of clamping abutments (24), (34), when the upper arm (20) is engaged by said catch members (52) and (62).

Optionally, said clamp (10), further comprises tube retainment means (74) at said second longitudinal ends (22), (32). Preferably, said tube retainment means (74) comprises an upper tab (76) and an opposed lower tab (78), said tabs (76) and (78) being resilient and depending from corresponding free edges, (26) and (36) respectively, of the said second longitudinal ends (22), (32) of said upper arm (20) and said lower arm (30), respectively. Said tabs (76), (78) form an entry section and defining a throat (79) therebetween, said throat (79) not being substantially wider than the maximum diameter of said range of diameters. In practice, the size of the throat (79) may be considerably smaller than the diameter of the tube (90). Thus, the throat (79) may be of a dimension just greater than twice the wall thickness of the tube (90), thereby permitting the tube (90) to be inserted therethrough by manually squeezing the tube (90) such that the tube is fully collapsed between the fingers. The said opposed tabs (76), (78), the said free edges (26), (36) of said second longitudinal ends (22) and (32), and a facing lateral edge (42) of said resilient base (40) thus define a substantially longitudinal, laterally open aperture (44) substantially larger than the maximum diameter of said predetermined range of diameters for enabling a tube having a diameter within said predetermined range of diameters to be accommodated therein. Advantageously, the perimeter of the said open aperture (44) is substantially C-shaped.

Optionally, the said tabs (76), (78) are in the form of suitable resilient U-shaped leaf springs. Preferably, though, said tabs (76), (78) substantially follow the profile of a corresponding parallel portion of said resilient base (40).

A third embodiment of the present invention, illustrated in FIG. 3, comprises the same elements and features as the preferred embodiemnt, as hereinbefore described, *mutatis mutandis*. Further, and in order to afford the capability of regulating the flow of fluid through a tube (90) held in said clamp (10), the said first catch arm (50) and said second catch arm (60) each comprise, in the third embodiment, a plurality of catch member, (52) and (62) respectively, each plurality of catch members arranged one above the other in the corresponding catch arm, as illustrated in FIG. 3. Typically, the catch arms (50) and (60) each comprise the same number of catch members (52) and (62) respectively, typically between 1 and 10 catch members on each catch arm. Advantageously, each of said plurality of catch members (52) of the first catch arm (50) is laterally aligned with the corresponding one of the plurality of catch members (62) of the said second catch arm (60). The said latching means (28) may then selectively engage with each corresponding pair of laterally aligned catch members (52), (62) to progressively reduce the magnitude of said third distance (d3), and enable a tube of a diameter within said predetermined range of diameters held between said clamping abutments to be correspondingly progressively collapsed. In particular, the lowermost pair of catch members (52), (62) may be strategically positioned to provide a third distance (d3) such that when the said latch means (28) is engaged therewith, the distance (d2) between the said clamping abutments (24), (34) is substantially reduced to the extend of ensuring that the tube (90) is totally collapsed between the clamping elements (24), (34), thereby interrupting any possible flow through the now-closed lumen (99) of the tube (90). In this manner, the flow rate of fluid flowing in the tube (90) may be regulated as well as completely terminated.

Optionally, and as illustrated in FIG. 3 for the third embodiment, said clamp (10) may further comprise an auxiliary catch member (80) on said at least one first catch arm (50), or alternatively on said at least second catch arm (60), or preferably on both said catch arms (50) and (60). The said latch means (28) on said first end (21) of said upper arm (20) is also adapted for selective engagement with said auxiliary catch member (80) within said first ends, (21) and (31), are at said predetermined first distance (d1) from each other, thereby preventing said upper and said lower arms, (20) and (30) respectively, from being spaced apart. Said auxiliary catch member (80) is typically similar to said catch member (50) in form and operation, *mutatis mutandis*.

Optionally, and as illustrated in FIGS. 2 and 3 for the preferred and third embodiments respectively, said clamp (10) may further comprise shear prevention means (85) for substantially preventing lateral movement between at least one of said at least one first catch arm (50) and said at least one second catch arm (60) relative to said upper arm (20).

As illustrated in FIG. 2, the said shear prevention means (85) in the preferred embodiment may comprise a pair of opposed tabs (87), (88) respectively at each lateral edge (82), (83) of said first end (21) of said upper arm (20), each said tab (87), (88) depending longitudinally from said first end (21), and being adapted to respectively engage a corresponding outer later edge, (68), (58) respectively, of the said second catch arm (60) and said first catch arm (50).

Alternatively, and as illustrated in FIG. 3 for the third embodiment, for example, the said shear prevention means (85) may optionally comprise a tab (86) at the said first end (21) of said upper arm (20) and substantially aligned with said slot (56), said tab (86) being adapted to engage either of the opposed sidewalls (59), (69) of the said first catch arm (50) and said second catch arm (60), respectively. While this arrangement has been described with respect to the third embodiemtn, it may be incorporated in the preferred embodiemnt in a similar manner as that described, *mutatis mutandis*. In such a case, the preferred embodiment would typically not also comprise the shear prevention means arrangement described with respect thereto above.

Figure 7A:
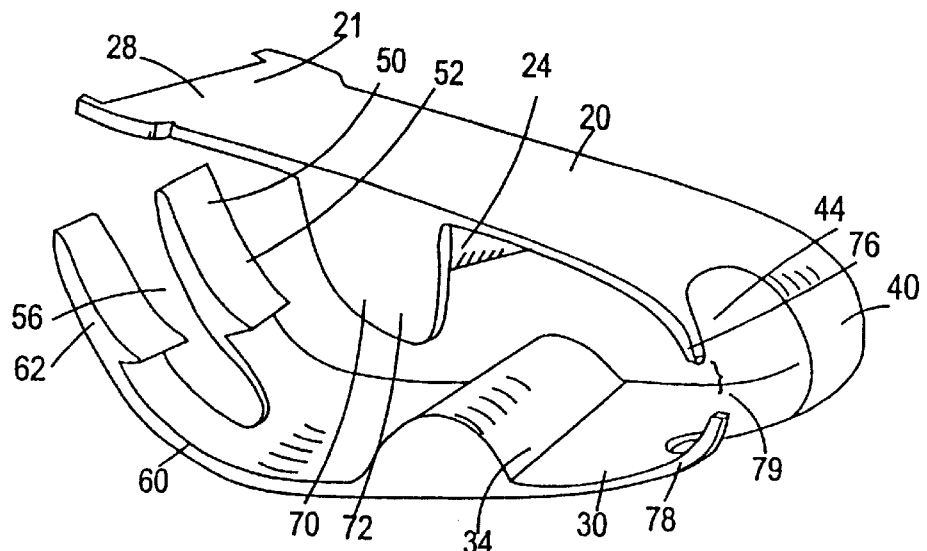
FIG. 7 illustrates, in perspective view, the operation of the embodiment of FIG. 2–FIG. 7(a)—clamp in the open configuration.
FIG. 7(b)—clamp in the closed configuration.
FIG. 7(c)—clamp in the closed configuration.
Figure 7B:
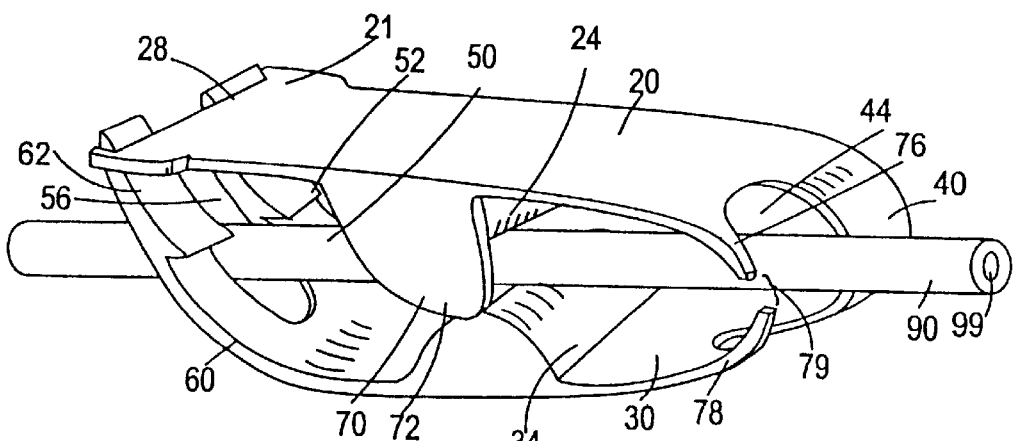
Figure 7C:
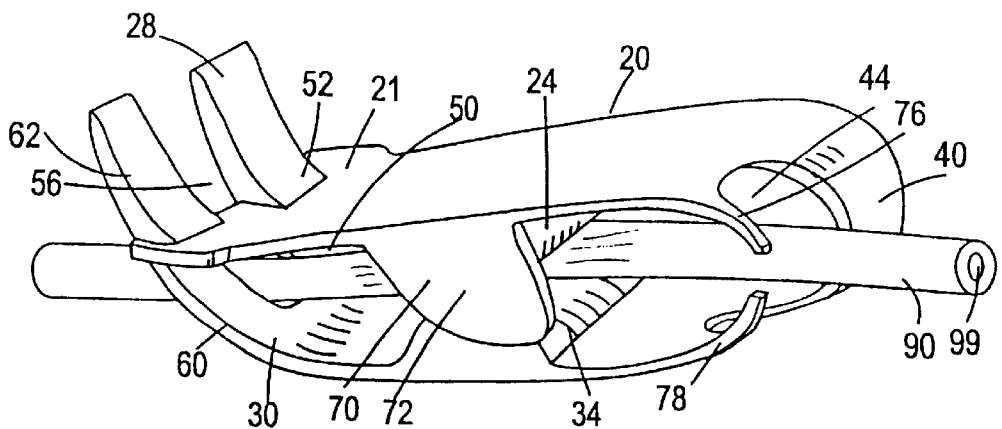

In the preferred embodiment of the present invention, and with reference to FIG. 7, the clamp (10) may be used as follows. To mount the clamp (10) onto suitable tubing, the upper and lower arms (20), (30) are first pulled apart until the lateral guard means (70), typically the said tab element (72) is sufficient clear from the opposed clamping abutment (in FIG. 7, the lower clamping abutment (34)) such that a middle section of the tube (90) may be laterally in between the clamping elements (24), (34), FIG. 7(*a*). Of course, the tab element (72) in practice need only clear the opposed clamping abutment (34) by a distance approximately equal to twice the thickness of the tube (90), since the latter, being flexible, may be squeezed together by hand in order to urge it into the clamp through the gap so produced. Concurrently, as the arms (20) and (30) are pulled apart, another portion of the tube (90) longitudinally displaced from the said middle section of the tube (90,), is inserted between the said first end (21) and the said arms (50), (60), in particular into the said slot (56). The resilience of the base (40) returns the upper and lower arms (20) and (30) to their original relative positions, with the first end (21) of the upper arm in close proximity to the catch arms (50) and (60). FIG. 7(*b*). In this closed, but unclamped position, the tube (90) is loosely held between the clamping abutments (24), (34), and is prevented from being laterally removed from the clamp (10) by the lateral guard means (70) on one side, and by the substantially closed slot (56). The tube (90) may be further prevented from being accidentally removed from the clamp (or vice versa), by inserting another section thereof, longitudinally displaced from said middle section of the tube (90), into the aperture (44) via said throat (79) formed between said tabs (76), (78). If the said throat (79) is narrower than external diameter of the tube (90), this may be manually squeezed and urged into the cavity (44) through the throat (79). When it is desired to clamp the said tube (90), and thereby to restrict any possible flow therethrough, the said upper arm (20) is moved towards said lower arm (30) causing the catch arms (50) and (60) to be cammed outwardly from the latch means (28) enabling the latch means (28) to proceed downwardly below the catch members (52), (62) respectively whereupon the catch arms (50) and (60) swing towards the latch means (28) so that the end surface (29) engages the catch members (52) and (62), FIG. 7(*c*). To remove the tube (90) from the clamp (10) of the preferred embodiment, the catch arms (50) and (60) are pulled away from the said first end (21) of the upper arm (20) to disengage the latch means (28) from the catch members (52) and (62) respectively, the arms (20) and (30) are then pulled apart sufficiently to allow the tube to be laterally removed from the clamping abutments, in particular through the gap between the tab (72) and the opposed clamping abutment (34), and out of the slot (56). Finally, the other end of the tube (90) is pulled out of the cavity (44) via throat (79).

In the third embodiment of the present invention, the clamp (10) may be used in a similar manner as described with respect to the said preferred embodiment of the present invention, *mutatis mutandis*. Further, since the catch arms (50) and (60) are each provided with said auxiliary catch member (80), then the latter is disengaged from the latching means (28) prior to pulling apart the upper and lower arms (20), (30). Then, after the clamp (10) is mounted onto the tubing (90), the auxiliary catch members (80) on each arm (50), (60) are reengaged with the latching means (28) by bringing the upper and lower arms (20), (30) towards each other sufficiently such that the catch arms (50) and (60) are cammed outwardly from the latch means (28) enabling the latch means (28) to proceed downwardly below the auxiliary catch members (80), whereupon the catch arms (50), (60) each swing towards the latch means (28) so that the end surface (29) engages the auxiliary catch members (80). Also, since the catch arms (50) and (60) each comprise a plurality of catch members (52) and (53) the said latching means (28) may then selectively engage with each corresponding pair of laterally aligned catch members (52), (62) to progressively reduce the magnitude of said third distance (d3), and enable a tube of a diameter with said predetermined range of diameters held between said clamping abutments to be correspondingly progressively collapsed. Thus, if the arms (20) and (30) are distanced from each other such that the latch means (28) engages with an upper pair of clamping elements (24), (34), the distance (d2) between the said clamping abutments (24), (34) is correspondingly only partially reduced from (d3) to the extend of ensuring that the tube (90) is correspondingly partially collapsed between the clamping elements (24), (34), thereby reducing any possible flow through the lumen (99) of the tube (90). Further, if the arms (20) and (30) are brought sufficiently close together such that now the lowermost pair of catch members (52), (62) the engaged with the said latch means (28), the distance (d2) between the said clamping abutments (24), (34) is substantially reduced to the extent of ensuring that the tube (90) is totally collapsed between the clamping elements (24), (34), thereby interrupting any possible flow through the now-closed lumen (99) of the tube (90). In this manner, the flow rate of fluid flowing in the tube (9) may be regulated as well as completely terminated.

While in the foregoing description describes in detail only a few specific embodiments of the invention, it will be understood by those skilled in the art that the invention is not limited thereto and that other variations in form and details may be possible without departing from the scope and spirit of the invention herein disclosed.

What is claimed is:

1. A pinch clamp device for use with a resilient collapsible tube having an external diameter within a predetermined range of diameters comprising:
    a U-shaped body comprising a generally longitudinal upper arm and a generally longitudinal lower arm, said arms comprising opposed longitudinal first ends and opposed longitudinal second ends, said second longitudinal ends being joined to a resilient base biased to distance the said first ends of the arms apart by substantially a predetermined first distance;
    aligned clamping abutments disposed on at least a portion of facing surfaces of said upper and lower arms, said clamping abutments adapted for clamping therebetween a resilient collapsible tube having an external diameter within said predetermined range of diameters, wherein at least part of said aligned clamping abutments project laterally at least with respect to said base by at least a predetermined fourth distance sufficient to enable a resilient tube having an external diameter within said predetermined range of diameters to be clamped between said clamping abutments laterally with respect to said base, said predetermined first distance between said first ends being such as to provide a second distance between said clamping abutments at least equal to the largest diameter of said predetermined range of diameters;
    at least one first flexible catch arm extending generally upwardly from the first end of said lower arm and comprising at least one catch member, said at least one catch member generally facing said first end of said upper arm, said first catch arm being resiliently connected to said lower arm and biased to maintain at least an upper portion of said first catch arm in at least close proximity to said first end of said upper arm at least when said first ends are at said predetermined first distance apart;
    latch means on said first end of said upper arm adapted for selective engagement with said catch member when said first ends are at a predetermined third distance from each other, whereupon said second distance between said clamping abutments is correspondingly reduced thereby enabling a tube of a diameter within said predetermined range of diameters held between said clamping abutments to be at least partially collapsed.

2. A pinch clamp as claimed in claim 1, wherein said upper arm and said lower arm comprise suitable lateral extensions, wherein said extensions project laterally in the same direction and substantially to the same extend relative to the said base as said clamping abutments.

3. A pinch clamp as claimed in claim 2, wherein said lower arm further comprises at least one second flexible catch arm extending generally upwardly from the first end of said lateral extension of said lower arm and comprising at least one catch member, said at least one catch member generally facing said first end of said upper arm, said second catch arm being resiliently connected to said lower arm and biased to maintain at least an upper portion of said second catch arm in at least close proximity to said first end of said upper arm at least when said first ends are at said predetermined first distance apart, said second catch arm being laterally displaced from said at least one first catch arm to define a slot therebetween having a predetermined width.

4. A pinch clamp as claimed in claim 3, wherein said predetermined width is at least equal to the largest diameter of said predetermined range of diameters.

5. A pinch clamp as claimed in claim 3, wherein the lower longitudinal end of said slot is substantially rounded.

6. A pinch clamp as claimed in claim 3, further comprising an auxiliary catch member on said second catch arm wherein said latch means on said first end of said upper arm is adapted for selective engagement with said auxiliary catch member when said first ends are at a predetermined first distance from each other, thereby selectively preventing said upper and said lower arms from being spaced apart.

7. A pinch clamp as claimed in claim 3, further comprising tube retainment means at said second longitudinal ends.

8. A pinch clamp as claimed in claim 7, wherein said tube retainment means comprises an upper tab and an opposed lower tab, said tabs being resilient and depending from corresponding free edges of the said second longitudinal ends of said upper arm and said lower arm, respectively, said tabs forming an entry section and defining a throat therebetween, said throat not being substantially wider than the maximum diameter of said range of diameters, said opposed tabs and said free edges of said second longitudinal ends and a facing lateral edge of said resilient base defining a substantially longitudinal open aperture for receiving a tube having a diameter within said predetermined range of diameters.

9. A pinch clamp device as claimed in claim 8 wherein said latch means comprises an end surface adapted for selective engagement with said at least one catch member, said latch means and said at least one catch member comprising cooperating cam surfaces on the engaging portions of the said latch means and catch arm, whereby selective movement of said upper arm towards said lower arm causes the catch arm to be cammed outwardly from the latch means enabling the latch means to proceed downwardly below the catch member whereupon the catch arm swings towards the latch means so that the end surface engages the at least one catch member.

10. A pinch clamp device as claimed in claim 8, wherein said tabs are in the form of suitable resilient U-shaped leaf springs.

11. A pinch clamp device as claimed in claim 8, wherein said tabs substantially follow the profile of a corresponding parallel portion of said resilient base.

12. A pinch clamp device as claimed in claim 8, wherein the perimeter of the said open aperture is substantially C-shaped.

13. A pinch member as claimed in claim 9, wherein said catch member comprises an engaging surface for engaging with said end surface of said at least one catch member, said engaging surface being aligned in a lateral direction with respect to said upper arm.

14. A pinch clamp device as claimed in claim 1, wherein said third distance is such as to enable a tube of a diameter within said predetermined range of diameters to be fully collapsed when in-between said clamping abutments, thereby preventing any fluid from flowing through such a tube.

15. A pinch clamp as claimed in claim 1, further comprising an auxiliary catch member on said at least one first catch arm wherein said latch means on said first end of said upper arm is adapted for selective engagement with said auxiliary catch member when said first ends are at a predetermined first distance from each other, thereby selectively preventing said upper and said lower arms from being spaced apart.

16. A pinch clamp as claimed in claim 1, further comprising shear prevention means for substantially preventing lateral movement between at least one of said at least one first catch arm and said at least one second catch arm relative to said upper arm.

17. A pinch clamp as claimed in claim 16, wherein said shear prevention means comprises a tab at the said first end of said upper arm, said tab being adapted to engage either of the sidewalls of the said slot between said first and said second catch arms.

18. A pinch clamp as claimed in claim 16, wherein said shear prevention means comprises a pair of opposed tabs at opposite lateral edges of said first end of said upper arm, each said tab being adapted to respectively engage a corresponding outer lateral edge of the said first and said second catch arms.

19. A pinch clamp device as claimed claim 1, wherein said clamping abutments comprise lateral guard means for preventing a tube of a diameter within said predetermined range of diameters positioned between said clamping abutments from being laterally removed therefrom when said clamping abutments are distanced from each other at said predetermined second distance.

20. A pinch clamp device as claimed in claim 19, wherein said lateral guard means comprises at least one tab element projecting from one said clamping abutment in the direction of the facing clamping abutment, said tab element adapted to laterally overlap said facing clamping abutment when said latch means is engaged with said at least one catch member.

* * * * *

UNITED STATES PATENT AND TRADEMARK OFFICE
CERTIFICATE OF CORRECTION

PATENT NO. : 6,234,448 B1
DATED : May 22, 2001
INVENTOR(S) : Gad Porat

Page 1 of 1

It is certified that error appears in the above-identified patent and that said Letters Patent is hereby corrected as shown below:

Title page,
Item [56], References Cited, the following reference "88 12 121   1/1989  (DE)" should read -- 88 12 121.6    1/1989   (DE) --.

Column 16, claim 19,
Line 14, "as claimed claim 1, wherein" should read -- as claimed in claim 1, wherein --.

Signed and Sealed this

Nineteenth Day of February, 2002

Attest:

JAMES E. ROGAN
*Attesting Officer*     *Director of the United States Patent and Trademark Office*

UNITED STATES PATENT AND TRADEMARK OFFICE
CERTIFICATE OF CORRECTION

PATENT NO. : 6,234,448 B1  
DATED : May 22, 2001  
INVENTOR(S) : Gad Porat

Page 1 of 1

It is certified that error appears in the above-identified patent and that said Letters Patent is hereby corrected as shown below:

<u>Column 16, claim 19,</u>  
Line 14, "as claimed claim 1, wherein" should read -- claimed in claim 1, wherein --

This certificate supersedes Certificate of Correction issued February 19, 2002.

Signed and Sealed this

Twelfth Day of March, 2002

Attest:

*Attesting Officer*

JAMES E. ROGAN  
*Director of the United States Patent and Trademark Office*